United States Patent
Sonkusale et al.

(10) Patent No.: US 9,459,375 B2
(45) Date of Patent: Oct. 4, 2016

(54) ACTIVE MANIPULATION OF ELECTROMAGNETIC WAVE PROPAGATION IN METAMATERIALS

(75) Inventors: Sameer Sonkusale, Arlington, MA (US); Willie John Padilla, Newton, MA (US); Saroj Rout, Nashua, NH (US)

(73) Assignees: TUFTS UNIVERSITY, Medford, MA (US); TRUSTEES OF BOSTON COLLEGE, Chestnut Hill, MA (US)

( * ) Notice: Subject to any disclaimer, the term of this patent is extended or adjusted under 35 U.S.C. 154(b) by 167 days.

(21) Appl. No.: 13/883,442

(22) PCT Filed: Nov. 1, 2011

(86) PCT No.: PCT/US2011/058721
§ 371 (c)(1),
(2), (4) Date: Dec. 11, 2013

(87) PCT Pub. No.: WO2012/061345
PCT Pub. Date: May 10, 2012

(65) Prior Publication Data
US 2014/0085711 A1    Mar. 27, 2014

Related U.S. Application Data

(60) Provisional application No. 61/410,461, filed on Nov. 5, 2010.

(51) Int. Cl.
*H03B 28/00* (2006.01)
*G02B 1/00* (2006.01)
*H01P 7/08* (2006.01)
*G01N 21/3581* (2014.01)

(52) U.S. Cl.
CPC .............. *G02B 1/002* (2013.01); *H01P 7/082* (2013.01); *H01P 7/088* (2013.01); *G01N 21/3581* (2013.01)

(58) Field of Classification Search
USPC ........................................................ 331/65
See application file for complete search history.

(56) References Cited

U.S. PATENT DOCUMENTS

| | | | |
|---|---|---|---|
| 7,525,711 | B1 | 4/2009 | Rule et al. |
| 7,683,444 | B2 | 3/2010 | Tonucci |
| 2007/0188385 | A1 | 8/2007 | Hyde et al. |
| 2010/0134215 | A1 | 6/2010 | Lee et al. |
| 2010/0301971 | A1* | 12/2010 | Yonak et al. ............. 333/219.1 |
| 2013/0240251 | A1* | 9/2013 | Kaplan et al. ............. 174/254 |

* cited by examiner

*Primary Examiner* — Joseph Chang
(74) *Attorney, Agent, or Firm* — Occhiuti & Rohlicek LLP

(57) ABSTRACT

An apparatus for controlling propagation of an electromagnetic wave includes a metamaterial having an array of cells, each cell containing a metallic structure having a resonant frequency; a plurality of devices integrated in the metamaterial, each of said devices being in electrical communication with a metallic structure in a cell in the array of cells; and a controller for electrically activating each of said plurality of devices to cause said resonant frequency to change, thereby causing at least one of a permeability and permittivity of the metamaterial to change.

23 Claims, 4 Drawing Sheets

ACTIVE MANIPULATION OF ELECTROMAGNETIC WAVE PROPAGATION IN METAMATERIALS

CROSS REFERENCE TO RELATED APPLICATIONS

This application is a National Stage of International Application No. PCT/US2011/058721 filed on Nov. 1, 2011, which claims the priority of U.S. provisional application No. 61/410,461 filed on Nov. 5, 2010, the contents of which are incorporated by reference in their entirety.

FIELD OF DISCLOSURE

This disclosure relates to the real-time control of electromagnetic wave propagation, and in particular, to the control of electromagnetic waves propagating in a metamaterial.

BACKGROUND

Between the optical frequencies and the microwave frequencies is a broad expanse of spectrum in the terahertz range. However, development of devices for operation in the terahertz range is hampered, to some extent, by a dearth of devices for manipulating or detecting terahertz waves.

Terahertz radiation is useful for a variety of purposes, including security systems. Because of its ability to penetrate most clothing, terahertz radiation provides a way to detect concealed weapons. Another use for terahertz radiation arises in the context of cancer treatment. Because of its ability to detect differences in water content and density of tissue, terahertz radiation can be used to reliably distinguish between normal cells and cancerous cells.

Electromagnetic metamaterials for supporting propagation of a particular wavelength consist of composites having a patterned metallic structure having dimensions on the order of the wavelength to be propagated. The interaction of these metallic structures with the surrounding medium results in a wave propagation medium that can have negative values of permittivity and/or permeability.

SUMMARY

The invention is based in part on the recognition that the dimensions associated with terahertz structures are similar to those of features made with conventional integrated circuit fabrication techniques.

In one aspect, the invention features an apparatus for controlling propagation of an electromagnetic wave. Such an apparatus includes a metamaterial having an array of cells, each cell containing a metallic structure having a resonant frequency; a plurality of devices integrated in the metamaterial, each of said devices being in electrical communication with a metallic structure in a cell in the array of cells; and a controller for electrically activating each of said plurality of devices to cause said resonant frequency to change, thereby causing at least one of a permeability and permittivity of the metamaterial to change.

In some embodiments, the plurality of devices comprise transistors. Among these embodiments are those that have at least one pHEMT.

In other embodiments, the device comprises a diode.

Additional embodiments include those in which the controller is configured to cause at least one electromagnetic parameter of the metamaterial to assume a negative value, those in which the controller is configured to modify an imaginary part of at least one electromagnetic parameter of the metamaterial, and those in which the controller is configured to modify an real part of at least one electromagnetic parameter of the metamaterial.

Also among the embodiments of the apparatus are those in which the controller is configured to cause said resonant frequency to sweep across a range of values, as well as those in which the controller is configured to dynamically vary a transmission coefficient of the metamaterial.

Embodiments of the apparatus include those in which the controller is configured to cause modulation of a signal. Among these are those in which the controller is configured to cause amplitude modulation of a signal, those in which the controller is configured to cause frequency modulation of a signal, those in which the controller is configured to cause phase modulation of a signal, and even those in which the controller is configured to modulate a signal by frequency-shift keying.

In some embodiments of the apparatus, the metallic structures have a dimension that is within the terahertz range of wavelengths as measured in the metamaterial.

Other embodiments include those having a terahertz source configured to illuminate said metamaterial and those having a terahertz detector configured to receive terahertz waves that have passed through said metamaterial.

In another aspect, the invention features a method for manipulating an electromagnetic wave passing through a metamaterial. Such a method includes causing an electromagnetic wave to propagate in said metamaterial; and at each of a plurality of locations in the metamaterial, dynamically changing at least one of a permittivity and a permeability of the metamaterial.

Specific practices of the foregoing method include those in which changing at least one of the permittivity and permeability comprises dynamically changing a resonant frequency of a metallic structure embedded within the metamaterial; those in which dynamically changing comprises dynamically tuning a resonant frequency of an LC circuit equivalent to a metallic structure embedded within the metamaterial; those in which dynamically changing comprises applying a gate current to a plurality of transistors, each of which is connected to a metallic structure within the metamaterial; and those in which dynamically changing comprises causing one of said permittivity and permeability to become negative, thereby attenuating said electromagnetic wave.

Yet other practices of the method include those in which causing an electromagnetic wave to propagate comprises causing a terahertz wave to propagate in said metamaterial.

These and other features of the invention will be apparent from the following detailed description and the accompanying figures, in which:

DETAILED DESCRIPTION

Electromagnetic waves are known to propagate in various dielectric media. However, certain material properties of the material are known to significantly affect the propagation of electromagnetic waves. Specifically, each dielectric has a permittivity, which defines a ratio between the electric field (E) and the electric displacement (D), and a permeability that defines a ratio between the magnetic field (H) and magnetic flux density (B). Together, the permeability and permittivity define the phase velocity of a wave within the material, and the relative magnitudes of electric and magnetic field vectors in a wave propagating in the material. Because of their importance in defining the properties of electromagnetic wave propagation, the permittivity and permeability of a material will be collectively referred to herein as "electromagnetic parameters" for that material.

In general, electromagnetic parameters can be positive or negative, real, imaginary or complex. In some cases, electromagnetic parameters are scalars, whereas in others they are tensors.

Because of their effect on propagation characteristics, it is desirable to be able to control the electromagnetic parameters of a material. The methods and devices disclosed herein provide ways of controlling these properties in metamaterials for electromagnetic waves in the terahertz range in real-time.

Figure 1:
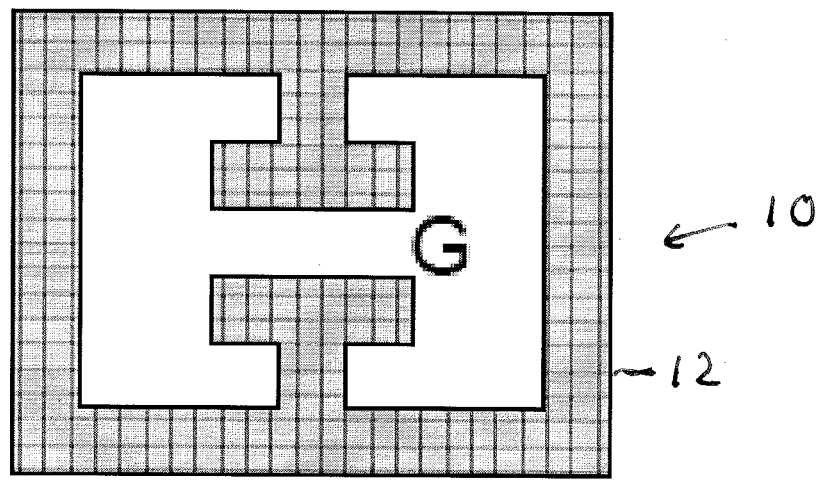
FIG. 1 shows a split-ring resonator.

Referring to FIG. 1, a metamaterial consists of an array of metamaterial unit cells 10. Each cell includes a metallic sub-wavelength structure. In the particular cell 10 shown, a conductor, preferably gold, defines a planar double-electric split-ring resonator 12. However, a metamaterial unit can have other types of metallic sub-wavelength structures. For example, instead of a split-ring resonator as shown, the metamaterial unit can have a split-ring structure with single and/or multiple loops, or a fishnet structure, or an arrangement of thin wires. In some embodiments, the metamaterial unit can include magnetodielectric spheres.

Figure 2:
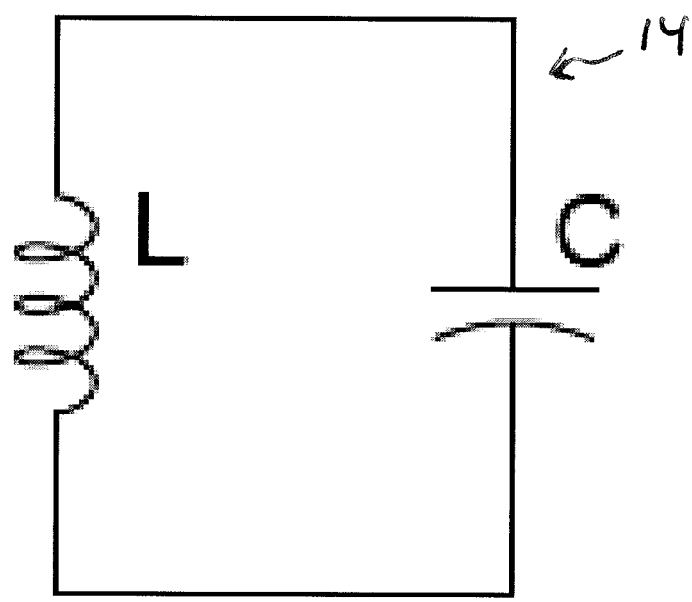
FIG. 2 is a first-order equivalent circuit for the resonator in FIG. 1.

A metamaterial unit cell 10, such as one with a split-ring resonator 12, is often electrically modeled as an LC resonant circuit 14, as shown in FIG. 2. The LC resonant circuit 14 shown in FIG. 2 is regarded as a first order circuit model because it omits any consideration of metamaterial losses. To achieve the desired metamaterial behavior, the equivalent inductance and capacitance of the split-ring resonator 12 are selected to cause resonance at any desired frequency, and for terahertz operation it could be set anywhere from 300 GHz around 100 THz. As is well known, tuning a split-ring resonator 12 to vary its equivalent inductance and capacitance is achieved by varying size and shape of its various constituent parts.

Figure 3:
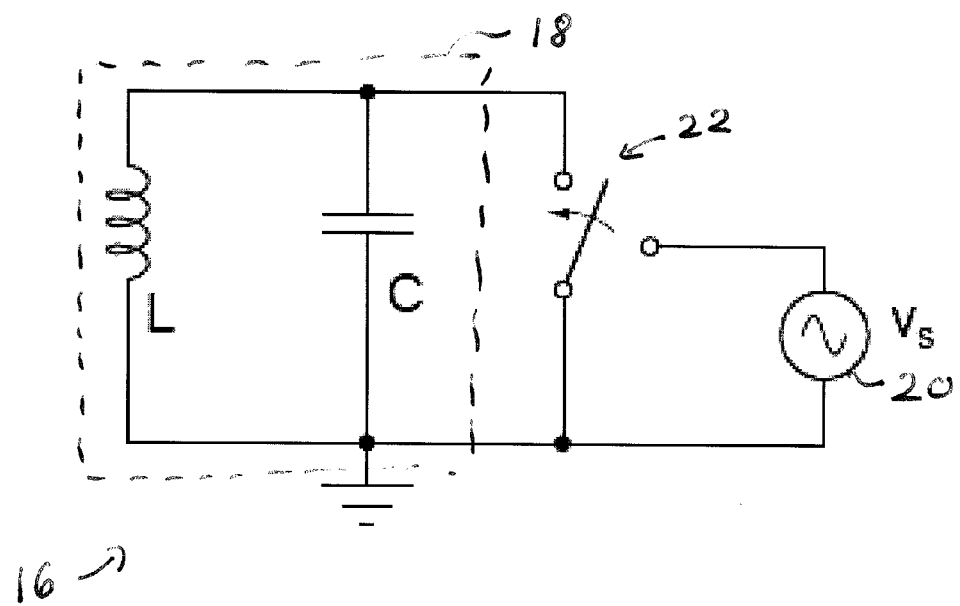
FIG. 3 is a first-order equivalent circuit for a shuntable resonator derived from the resonator in FIG. 2.

The permittivity of the metamaterial that includes cells 10 as shown in FIG. 1 can be perturbed by coupling a high speed switching device to each one of the split-ring resonators 12. Incorporation of such a switching device modifies the LC circuit 14 of FIG. 2 to yield a shuntable resonator circuit 16 as shown in FIG. 3, in which an LC resonator 18 is selectively tuned in and out of resonance from a voltage source 20 by a switch 22. Closing the switch 22 in the shuntable resonator circuit 16 effectively shunts, or shorts out the LC resonator 18. The collective response of such resonator circuits in the metamaterial lattice effectively provides a way to switch between two sets of electromagnetic parameters of the bulk metamaterial. Replacing the switch 22 with a variable resistance or a similar valve-like device allows continuous control of the electromagnetic parameters of the metamaterial. In an alternate arrangement, an embedded active electronic element, such as a transistor, tunes the effective capacitance and/or the effective inductance (i.e. the effective reactance) as a function of a tuning voltage $v_s$. This change in effective reactance causes a shift in resonant frequency as a function of the tuning voltage $v_s$.

Figure 4:
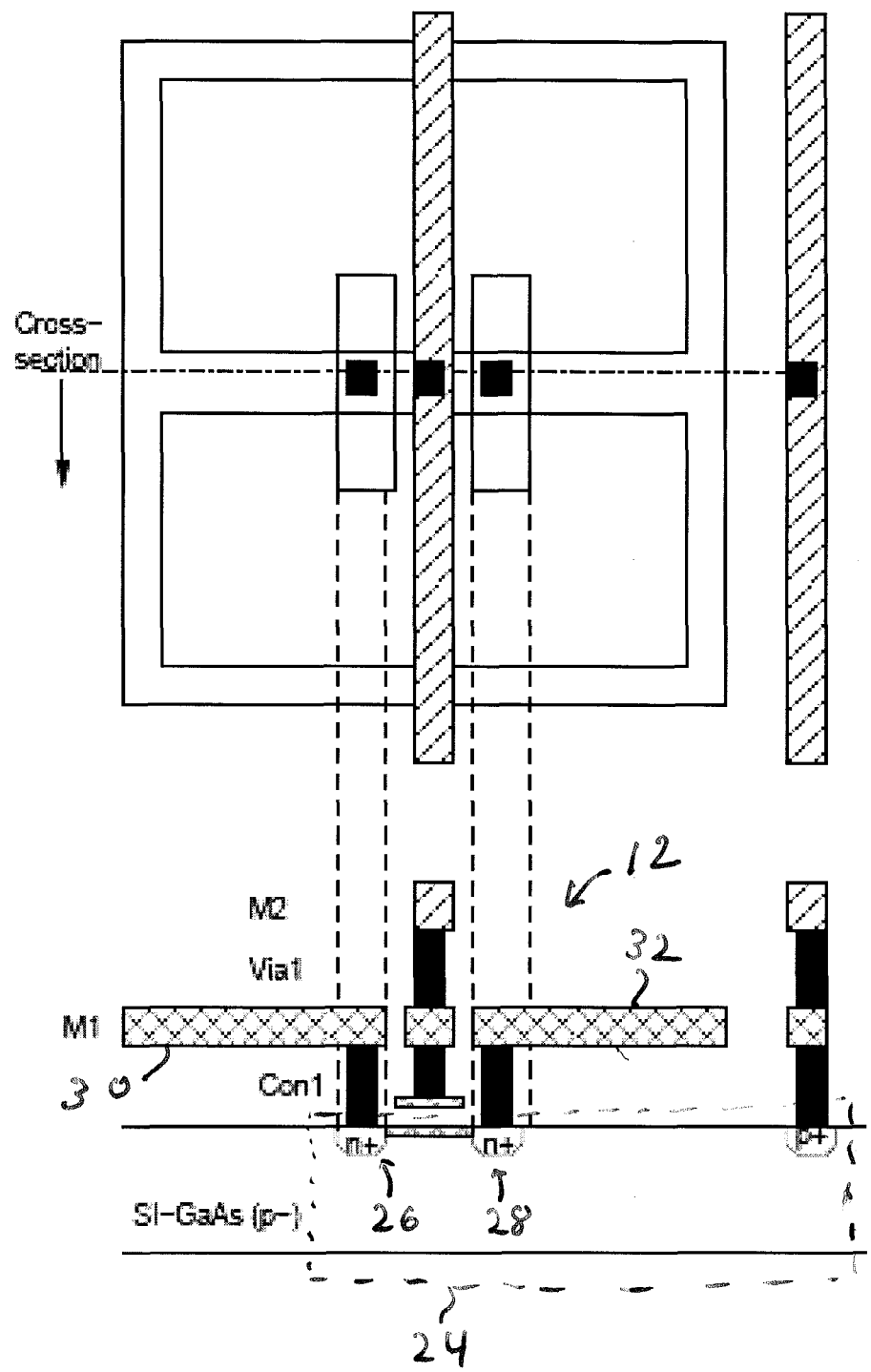
FIG. 4 shows a cell for a metamaterial having a split-ring resonator and a transistor.

FIG. 4 shows one implementation of the shuntable resonator circuit 16 of FIG. 3 in which a pHEMT 24 (pseudomorphic high electron mobility transistor) formed in a GaAs substrate lies below the split-ring resonator 12, with a drain 26 and source 28 of the transistor 24 connected to arms 30, 32 of the split-ring resonator 12.

Other embodiments rely on fabrication methods other than those used to incorporate a GaAs pHEMT with the resonator circuit element and the metamaterial in the metamaterial unit cell 10. Available options are silicon field effect transistor (FET), nanowire and nanotube FET, GaN HEMT, bipolar junction transistors (BJT), and heterojunction bipolar transistors (HBT).

Figure 5:
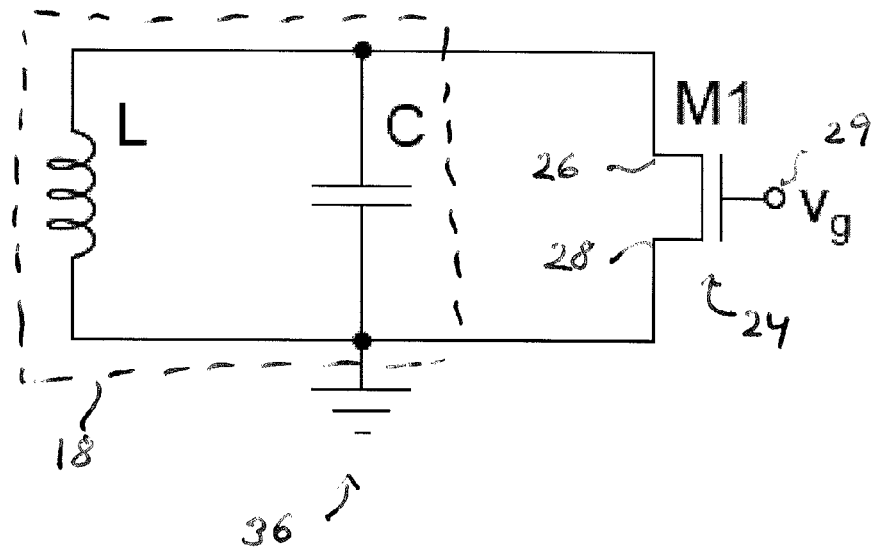
FIG. 5 is a first-order equivalent circuit for the structure in FIG. 4.

As shown in FIG. 5, an equivalent circuit 36 for the structure shown in FIG. 4 includes an LC resonator 18 in parallel with the transistor 24. A gate voltage $v_g$ at the gate 29 controls the source/drain current through the transistor 24. This gate voltage can be controlled to provide continuous or discrete variation in the source/drain or current of the transistor 24. Accordingly, it is possible to use the gate voltage to tune the metamaterial by varying its electromagnetic parameters in real-time An arrangement as shown in FIGS. 4 and 5 thus permits modulation of electromagnetic waves propagating in the metamaterial. This arises because when one of either permittivity or permeability become negative, the amplitude of a wave travelling through the metamaterial is reduced. Thus, there exists a basis for amplitude modulation of a terahertz wave using a metamaterial having multiple cells 10, each one of which is characterized by the circuit 36 shown in FIG. 5.

Figure 6:
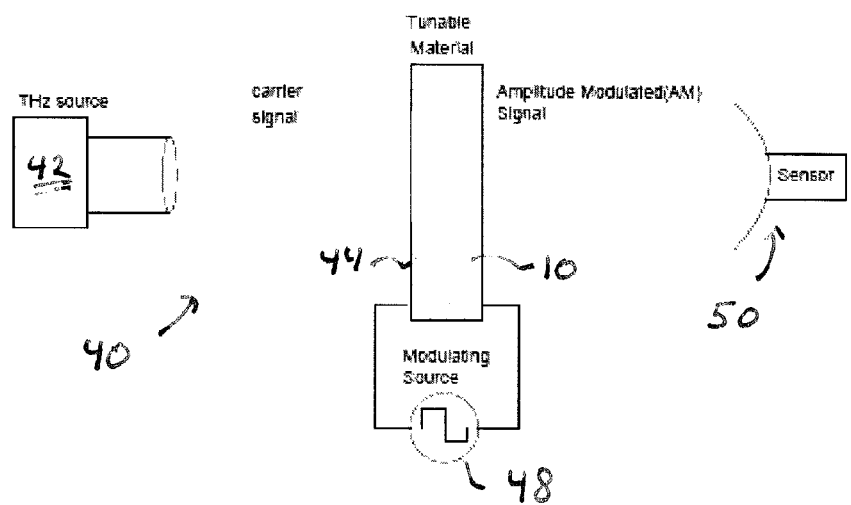
FIG. 6 is a terahertz modulation system using a metamaterial having cells as shown in FIG. 4.

FIG. 6 shows a modulation system 40 having a terahertz source 42 that outputs a carrier wave incident on a metamaterial 44 having an array of cells 10, each of which is characterized by the circuit 36 of FIG. 5. A modulating source 48 controls the gate terminals of each cell 10. As the carrier wave propagates through the metamaterial 44, the modulating source 48 impresses a signal upon it. The resulting modulated carrier wave, now carrying an amplitude modulated signal, then proceeds toward a terahertz sensor 50.

While the particular embodiment described herein is described in the context of terahertz frequencies, it should be recognized that the integration of a switching device into a metamaterial to control electromagnetic properties of the material is not limited to any particular frequency range. The terahertz range is described specifically because techniques for fabricating devices are well-suited to fabrication of device having features whose dimensions are comparable to terahertz wavelengths.

In the embodiment described herein, a split-ring resonator 12 forms the cell 10. However, the general principles described herein are not limited to any particular form of a cell 10. As one of ordinary skill in the art would recognize, any metallic structure will have some equivalent inductance and capacitance that can be effectively controlled or shorted out by suitable use of a switching device.

Additionally, although the devices disclosed herein rely on a pHEMT transistor as a switching device, such a device is used primarily for convenience. In fact, many other switching devices, for example diodes, could also be used to achieve the same result.

Amplitude modulation as described herein is achieved by varying the imaginary part of the permittivity and/or permeability of the metamaterial. However, in some embodiments, the real part can be varied. In these applications, the metamaterial can be used for phase modulation and/or frequency modulation.

Values of permeability and permittivity also control the reflection coefficient of an interface between the metamaterial and an adjoining propagation medium, such as free space. In other words, the extent to which a wave incident on a metamaterial will be reflected from or transmitted through the metamaterial depends on the values of the permeability and permittivity of the metamaterial. To the extent one can dynamically control these values, one can also achieve dynamic control over reflection and transmission coefficients. This allows creation of dynamically variable frequency-selective surfaces that can be tuned in real time to either transmit or reflect selected waves that are incident upon them.

The ability to actively tune a metamaterial by dynamically controlling its electromagnetic parameters enables fabrication of a filter that allows transmission of only selected wavelengths at selected times. For example, one could place such a material between a broadband terahertz source and a terahertz detector, and cause it to sweep across a range of wavelengths. This would result in a simple terahertz spectrometer with high spectral definition.

Having described the invention, and a preferred embodiment thereof, what we claim as new and secured by Letters Patent is:

1. An apparatus for controlling propagation of an electromagnetic wave, said apparatus comprising: a metamaterial having an array of cells, each cell containing a metallic structure having a resonant frequency; a plurality of devices integrated in the metamaterial, each of said devices being in electrical communication with a metallic structure in a cell in the array of cells; and a controller for electrically activating each of said plurality of devices to cause said resonant frequency to change, thereby causing at least one of a permeability and permittivity of the metamaterial to change.

2. The apparatus of claim 1, wherein the plurality of devices comprises a plurality of transistors.

3. The apparatus of claim 2, wherein the plurality of transistors comprises at least one pHEMT.

4. The apparatus of claim 1, wherein the plurality of devices comprises a diode.

5. The apparatus of claim 1, wherein the controller is configured to cause at least one electromagnetic parameter of the metamaterial to assume a negative value.

6. The apparatus of claim 1, wherein the controller is configured to modify an imaginary part of at least one electromagnetic parameter of the metamaterial.

7. The apparatus of claim 1, wherein the controller is configured to modify a real part of at least one electromagnetic parameter of the metamaterial.

8. The apparatus of claim 1, wherein the controller is configured to cause said resonant frequency to sweep across a range of values.

9. The apparatus of claim 1, wherein the controller is configured to dynamically vary a transmission coefficient of the metamaterial.

10. The apparatus of claim 1, wherein the controller is configured to cause modulation of a signal.

11. The apparatus of claim 10, wherein the controller is configured to cause amplitude modulation of a signal.

12. The apparatus of claim 10, wherein the controller is configured to cause frequency modulation of a signal.

13. The apparatus of claim 10, wherein the controller is configured to cause phase modulation of a signal.

14. The apparatus of claim 10, wherein the controller is configured to modulate a signal by frequency-shift keying.

15. The apparatus of claim 1, wherein the metallic structures have a dimension that is within the terahertz range of wavelengths as measured in the metamaterial.

16. The apparatus of claim 1, further comprising a terahertz source configured to illuminate said metamaterial.

17. The apparatus of claim 16, further comprising a terahertz detector configured to receive terahertz waves that have passed through said metamaterial.

18. A method for manipulating an electromagnetic wave passing through a metamaterial having an array of cells, each of which contains a metallic structure having a resonant frequency and a plurality of devices integrated therein, each of said devices being in electrical communication with a metallic structure in one of said cells, said method comprising: causing an electromagnetic wave to propagate in said metamaterial; and each of a plurality of locations in the metamaterial, dynamically changing at least one of a permittivity and a permeability of the metamaterial by electrically activating each of said devices, thereby changing a resonant frequency of a corresponding metallic structure.

19. The method of claim 18, wherein changing at least one of the permittivity and permeability comprises dynamically changing a resonant frequency of a metallic structure embedded within the metamaterial.

20. The method of claim 18, wherein dynamically changing comprises dynamically tuning a resonant frequency of an LC circuit equivalent to a metallic structure embedded within the metamaterial.

21. The method of claim 18, wherein dynamically changing comprises applying a gate current to a plurality of transistors, each of which is connected to a metallic structure within the metamaterial.

22. The method of claim 18, wherein causing an electromagnetic wave to propagate comprises causing a terahertz wave to propagate in said metamaterial.

23. The method of claim 18, wherein dynamically changing comprises causing one of said permittivity and permeability to become negative, thereby attenuating said electromagnetic wave.

* * * * *

UNITED STATES PATENT AND TRADEMARK OFFICE
CERTIFICATE OF CORRECTION

PATENT NO. : 9,459,375 B2
APPLICATION NO. : 13/883442
DATED : October 4, 2016
INVENTOR(S) : Sameer Sonkusale et al.

Page 1 of 1

It is certified that error appears in the above-identified patent and that said Letters Patent is hereby corrected as shown below:

In the Specification

At Column 1, Line 13, insert:
--GOVERNMENT SUPPORT
This invention was made with government support under grant number N00014-09-1-1075 awarded by the United States Navy. The government has certain rights in the invention.--

Signed and Sealed this
Tenth Day of December, 2019

Andrei Iancu
*Director of the United States Patent and Trademark Office*